(12) United States Patent
O'Donovan

(10) Patent No.: US 12,721,630 B2
(45) Date of Patent: Sep. 1, 2026

(54) VASCULAR OCCLUSION DEVICE

(71) Applicant: BOSTON SCIENTIFIC SCIMED, INC., Maple Grove, MN (US)

(72) Inventor: Joseph O'Donovan, Cork (IE)

(73) Assignee: Boston Scientific Scimed, Inc., Maple Grove, MN (US)

(*) Notice: Subject to any disclaimer, the term of this patent is extended or adjusted under 35 U.S.C. 154(b) by 129 days.

(21) Appl. No.: 18/212,894

(22) Filed: Jun. 22, 2023

(65) Prior Publication Data

US 2023/0414223 A1 Dec. 28, 2023

Related U.S. Application Data

(60) Provisional application No. 63/366,914, filed on Jun. 23, 2022.

(51) Int. Cl.
*A61B 17/12* (2006.01)
*A61B 17/00* (2006.01)

(52) U.S. Cl.
CPC .. *A61B 17/12145* (2013.01); *A61B 17/12109* (2013.01); *A61B 17/1215* (2013.01); *A61B 2017/00867* (2013.01); *A61B 2017/1205* (2013.01)

(58) Field of Classification Search
CPC ........ A61B 17/12145; A61B 17/12109; A61B 17/1215; A61B 2017/00867; A61B 2017/1205; A61B 17/12113; A61B 17/1214; A61F 2230/0091; A61F 2/88; A61F 2230/001
See application file for complete search history.

(56) References Cited

U.S. PATENT DOCUMENTS 5,382,260 A 1/1995 Dormandy, Jr. et al.
6,024,765 A 2/2000 Wallace et al.
6,929,654 B2 8/2005 Teoh et al.
7,955,344 B2 * 6/2011 Finitsis ............ A61B 17/32056 606/159
8,425,550 B2 4/2013 Elliott et al.
(Continued)

FOREIGN PATENT DOCUMENTS

EP 0587782 A1 4/1999
JP H10328191 A 12/1998

OTHER PUBLICATIONS

International Search Report and Written Opinion dated Oct. 16, 2023 for International Application No. PCT/US2023/025948.

*Primary Examiner* — Kathleen S Holwerda
*Assistant Examiner* — James R McGinnity
(74) *Attorney, Agent, or Firm* — Seager, Tufte & Wickhem LLP

(57) ABSTRACT

A vascular occlusion device includes an embolic device configured to be slidably received within and deployed from a catheter. The embolic device includes a wire having a primary shape when disposed within the catheter, and a secondary shape when released from the catheter. The primary shape is defined by a plurality of loops in a linearly expanded configuration, where all of the plurality of loops are longitudinally spaced apart and include upper loops and lower loops. In the secondary shape the upper loops are in a longitudinally overlapping configuration and the lower loops are in a longitudinally overlapping configuration.

20 Claims, 5 Drawing Sheets

(56) References Cited

U.S. PATENT DOCUMENTS

| | | | | |
|---|---|---|---|---|
| 8,870,908 | B2 * | 10/2014 | Labdag | A61B 17/12022 606/200 |
| 9,011,480 | B2 | 4/2015 | Divino et al. | |
| 10,524,799 | B2 | 1/2020 | O'Connor et al. | |
| 11,202,699 | B2 | 12/2021 | Yair et al. | |
| 2005/0277978 | A1 * | 12/2005 | Greenhalgh | A61B 17/1219 606/200 |
| 2008/0183203 | A1 * | 7/2008 | Fitzgerald | A61B 17/12136 606/198 |
| 2009/0054905 | A1 | 2/2009 | Levy | |
| 2010/0222803 | A1 | 9/2010 | Seifert et al. | |
| 2018/0303487 | A1 | 10/2018 | Tassoni et al. | |
| 2020/0078024 | A1 * | 3/2020 | Tekulve | A61B 17/1214 |
| 2020/0383689 | A1 * | 12/2020 | Ashurst | A61B 17/12109 |

* cited by examiner 14
12

14
17
16
12
13
5
17
D1

VASCULAR OCCLUSION DEVICE

CROSS-REFERENCE TO RELATED APPLICATIONS

This application claims the benefit of priority of U.S. Provisional Application No. 63/366,914 filed Jun. 23, 2022, the entire disclosure of which is hereby incorporated by reference.

TECHNICAL FIELD

The disclosure pertains to medical devices and more particularly to vascular occlusion devices, and methods for using such medical devices.

BACKGROUND

A wide variety of medical devices have been developed for medical use including, for example, medical devices utilized to occlude vessels in the treatment or prevention of pathological conditions. These medical devices may be used in a variety of vessels, and are manufactured and used according to any one of a variety of different methods. Of the known medical devices and methods, each has certain advantages and disadvantages. There is an ongoing need to provide alternative medical devices as well as alternative methods for manufacturing and using the medical devices.

SUMMARY

This disclosure provides design, material, manufacturing method, and use alternatives for medical devices. An example embolic device configured to be slidably received within and deployed from a catheter includes a single wire having a primary shape when disposed within the catheter, and a secondary shape when released from the catheter, wherein the primary shape is defined by a plurality of loops in a linearly expanded configuration, where all of the plurality of loops are longitudinally spaced apart and include upper loops extending above a longitudinal axis of the embolic device, and lower loops extending below the longitudinal axis, and wherein in the secondary shape the upper loops are in a longitudinally overlapping configuration and the lower loops are in a longitudinally overlapping configuration.

Alternatively or additionally to the embodiment above, in the secondary shape, the upper loops do not overlap the lower loops.

Alternatively or additionally to any of the embodiments above, the longitudinally overlapping configuration defines a series of longitudinally overlapping figure eights.

Alternatively or additionally to any of the embodiments above, the single wire is a helical coil of first loops, each of the first loops having a first outer diameter, each of the first outer diameters being substantially the same.

Alternatively or additionally to any of the embodiments above, the upper loops and the lower loops each have a second outer diameter larger than the first outer diameter, wherein each of the second outer diameters is substantially the same.

Alternatively or additionally to any of the embodiments above, the secondary shape is formed by longitudinally alternating upper and lower loops.

Alternatively or additionally to any of the embodiments above, at least some of the plurality of loops in the primary shape are open and define a serpentine shape.

Alternatively or additionally to any of the embodiments above, at least some of the plurality of loops in the primary shape are closed.

Alternatively or additionally to any of the embodiments above, the upper and lower loops in the secondary shape are all closed.

Alternatively or additionally to any of the embodiments above, the single wire automatically changes from the primary shape to the secondary shape when the wire is released from the catheter.

Alternatively or additionally to any of the embodiments above, the wire is made from nitinol.

Alternatively or additionally to any of the embodiments above, a cross section of the wire is round, and a diameter of the cross section is in a range of 0.05 mm to 0.3 mm.

Alternatively or additionally to any of the embodiments above, a distal end of the embolic device defines an atraumatic end, and a proximal end of the embolic device is devoid of any coupling element.

Alternatively or additionally to any of the embodiments above, the embolic device further includes multiple fiber bundles coupled to the wire.

An example vascular occlusion system includes a catheter having a lumen with a delivery end, and an embolic device configured to be slidably received within and deployed from the lumen of the catheter, the embolic device including a single wire having a primary shape when disposed in the lumen of the catheter, and a secondary shape when released from the delivery end, wherein the primary shape is defined by a plurality of loops in a linearly expanded configuration, where all of the plurality of loops are longitudinally spaced apart, wherein in the secondary shape the plurality of loops include upper and lower loops in a longitudinally overlapping configuration.

Alternatively or additionally to the embodiment above, the longitudinally overlapping configuration is a series of longitudinally overlapping figure eights.

Alternatively or additionally to any of the embodiments above, the secondary shape is formed by longitudinally alternating upper and lower loops.

Alternatively or additionally to any of the embodiments above at least some of the plurality of loops in the primary shape are open and define a serpentine shape.

Alternatively or additionally to any of the embodiments above at least some of the plurality of loops in the primary shape are closed.

Another example vascular occlusion system includes a catheter having a lumen with a delivery end, an embolic device configured to be slidably received within and deployed from the lumen of the catheter, the embolic device including a single wire having a primary shape when disposed in the lumen of the catheter, and a secondary shape when released from the delivery end, the primary shape defined by a plurality of loops in a linearly expanded configuration, where all of the plurality of loops are longitudinally spaced apart, wherein in the secondary shape the plurality of loops include upper and lower loops in a longitudinally overlapping configuration, and a pusher member disposed within the lumen, the pusher member having a distal end configured to push a proximal end of the embolic device out of the lumen, wherein the pusher member and the embolic device are not coupled.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figures 1A, 1B:
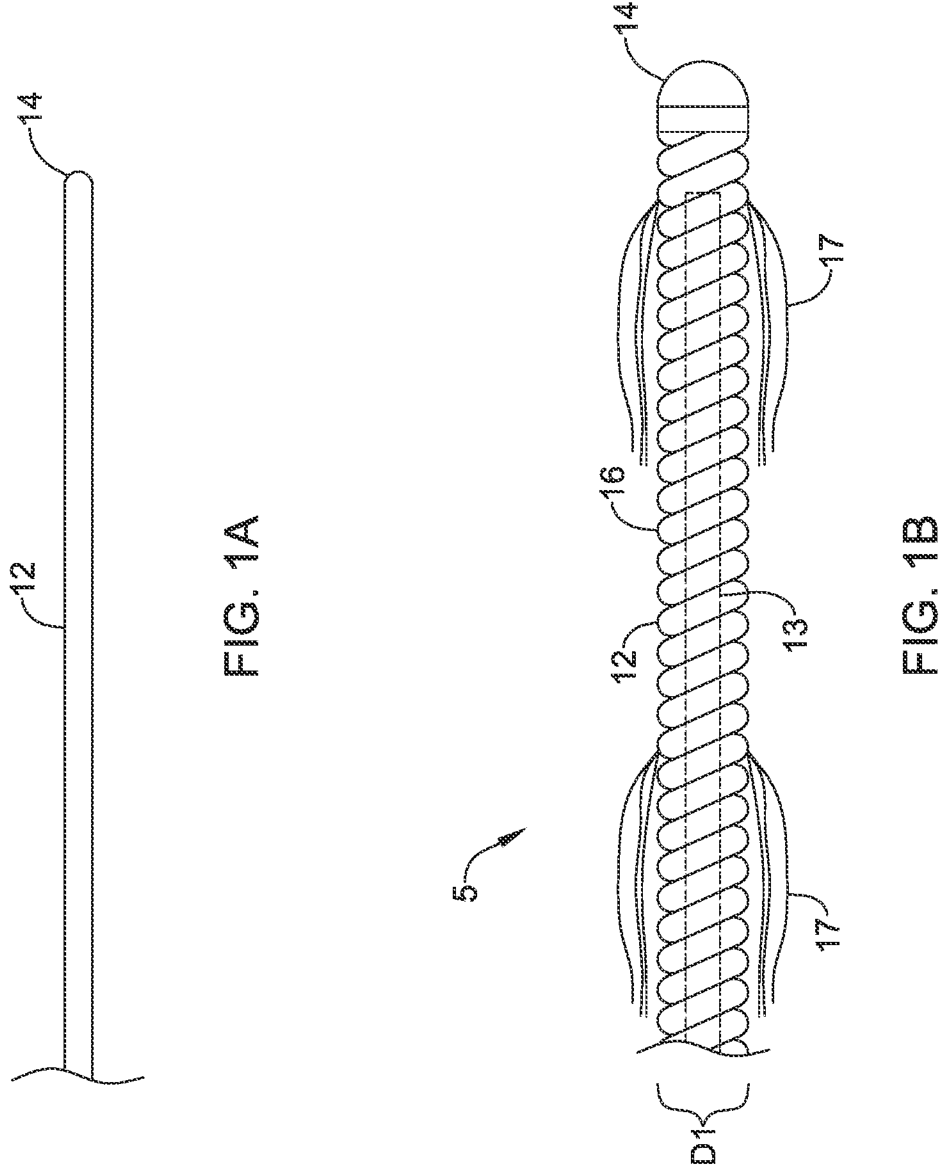
FIG. 1A is a side view of an example linear wire.
FIG. 1B is a side view of an example coiled wire.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "withdraw", variants thereof, and the like, may be generally considered with respect to the positioning, direction, and/or operation of various elements relative to a user/operator/manipulator of the device, wherein "proximal" and "withdraw" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc. Additionally, the term "substantially" when used in reference to two dimensions being "substantially the same" shall generally refer to a difference of less than or equal to 5%.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following description should be read with reference to the drawings, which are not necessarily to scale, wherein similar elements in different drawings are numbered the same. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

Many diseases or conditions may benefit from vascular occlusion, such as, but not limited to, bleeds, aneurysms, venous insufficiency, shutting off blood flow prior to organ resection, or preventing embolic bead reflux into branch vessels in the liver. Embolic devices can be used to close blood vessels and/or fill aneurysmal sacs to achieve vascular occlusion.

In some embodiments, a vascular occlusion device may include an embolic device made from a wire having a primary shape when disposed within a delivery catheter, and a secondary shape when released from the delivery catheter. The wire 12 may be a single, linear piece of wire with a rounded distal tip 14, as shown in FIG. 1A. In other embodiments, the wire 12 forming the embolic device may be a single wire wound multiple times to form a generally tubular structure such as a helical coil 5 with a rounded distal tip 14, as shown in FIG. 1B. The helical coil 5 may be formed from a series of contiguous loops or windings having a pitch that is constant or alternatively varies over the length of the helical coil 5. The helical coil 5 may be formed by a plurality of first loops 16 each having a first outer diameter D1. The first outer diameters D1 of the plurality of first loops 16 may be substantially the same, as illustrated in FIG. 1B, or they may be different. In some embodiments, a suture or inner wire 13 may be disposed at least partially within the helical coil 5. The suture or inner wire 13 may provide support, particularly when the helical coil 5 is formed from a soft wire 12.

In both embodiments shown in FIGS. 1A and 1B, the wire 12 may be formed with an atraumatic distal tip 14 that prevents damage to the vasculature of the patient while the embolic device traverses within the patient's vasculature. The distal tip 14 may be a rounded end of the wire 12. The distal end of the wire 12 may be ground to form a rounded, smooth end, or it may be heated to form a rounded end or ball. In other embodiments, the distal tip 14 may be made of non-radiopaque polypropylene. Alternatively, the distal tip 14 may serve as a distal implant marker enabling the embolic device to be placed in position under radiographic observance. In some embodiments, the distal tip 14 may be made of radiopaque material, such as a platinum/iridium alloy.

The wire 12 may be wound so as to form a primary shape when positioned in and constrained by a delivery catheter, and a secondary shape when released from the delivery catheter. The following description will refer to embolic devices 10, 100 made from a wire 12, 112, however it will be understood that the wire 12, 112 may be a single linear wire 12 as shown in FIG. 1A, or a single wire formed into a helical coil 5 as shown in FIG. 1B. In other embodiments, the wire 12 or helical coil 5 may be formed from a plurality of wires such as a braid or twisted bundle.

In some embodiments, a plurality of thrombogenic fiber bundles 17 may be attached to the wire 12, 112 or helical coil 5 at prescribed intervals to enhance coil thrombosis, as shown in FIG. 1B. In general, fiber bundles 17 include multiple fibers extending from a single attachment point as shown. However, in some embodiments, a single fiber can make up a fiber bundle. The fiber bundles 17 may be made of polyethylene terephthalate or nylon. Fiber bundles 17 are described in more detail in O'Connor et al., U.S. Pat. No. 10,524,799, the disclosure of which is incorporated herein by reference.

Figure 2:
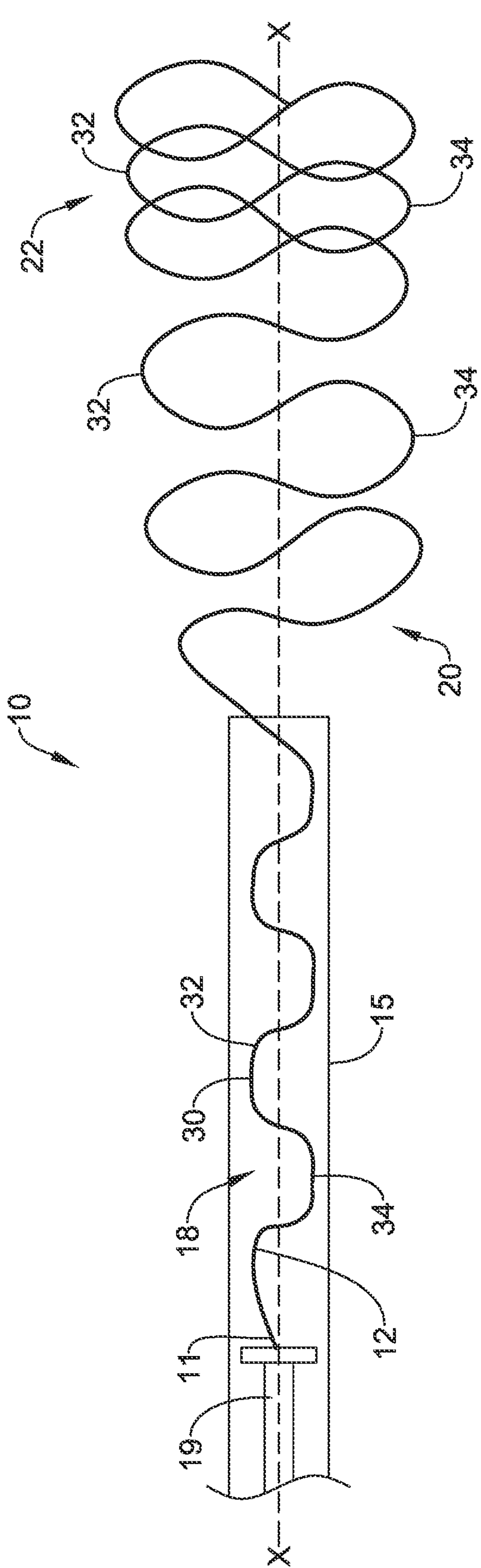
FIG. 2 is a side view of an example embolic device as it exits a delivery catheter and begins moving into the secondary shape, with the delivery catheter in cross-sectional view.

FIG. 2 illustrates the embolic device 10 with a proximal region 18 constrained in a primary shape within the lumen of a delivery catheter 15, a distal region 22 in a secondary shape outside the delivery catheter, and an intermediate region 20 transitioning from the primary shape to the secondary shape as the embolic device 10 exits the delivery catheter. In some embodiments, the embolic device 10 may be formed from a single wire 12 such that the entire embolic device is a monolithic structure. In other embodiments, the embolic device 10 may be formed from a plurality of wires 12 forming a plurality of secondary shapes. The wire 12 may automatically move from the primary shape to the predetermined secondary shape when the wire is released from the delivery end of the delivery catheter 15. For example, the wire 12 may be made of a nickel-titanium alloy (e.g., nitinol) which possesses both mechanical and thermal shape memory characteristics. In other embodiments, however, the wire 12 may be made of any material exhibiting mechanical and/or thermal shape memory characteristics or, alternatively, platinum, platinum alloys, tungsten, tungsten alloys, or other like materials. The wire 12 may be heat set or otherwise permanently set into the secondary shape such that it automatically transitions from the primary shape to the secondary shape as it exits the delivery catheter 15. In some embodiments, the wire 12 may have a round cross section, with a diameter in a range of 0.05 mm to 0.3 mm.

In the embodiment illustrated in FIG. 2, the proximal region 18 has a primary shape defined by a plurality of loops 30 in a linearly expanded configuration, where all of the plurality of loops are longitudinally spaced apart. The plurality of loops 30 includes upper loops 32 extending above a longitudinal axis X-X of the embolic device 10, and lower loops 34 extending below the longitudinal axis as illustrated in FIG. 2. At least some of the plurality of upper loops 32 and lower loops 34 in the primary shape are open and define a serpentine shape. This serpentine shape is defined by a series of undulating peaks (upper loops 32) and valleys (lower loops 34), as shown in the proximal region 18 and intermediate region 20. In the intermediate region 20, as the embolic device 10 exits the delivery catheter and begins to move into the secondary shape, the plurality of upper loops 32 move longitudinally closer together, and the plurality of lower loops 34 move longitudinally closer together. As shown in FIG. 2, the secondary shape is formed by longitudinally alternating upper loops 32 and lower loops 34. As the embolic device 10 continues moving distally beyond the delivery catheter 15, shown in the distal region 22, the plurality of upper loops 32 continue moving closer to one another until they longitudinally overlap one another, and the plurality of lower loops 34 continue moving closer to one another until they longitudinally overlap one another.

In some embodiments, a proximal end 11 and/or region of the wire 12 may be devoid of any coupling structure configured to be removably engaged with a delivery device. The proximal end of the wire 12 may be an atraumatic end ground into a round shape or melted into a ball similar to the distal tip 14 described above. Instead of using a coupling device to deliver the embolic device 10, the embolic device 10 is pushed out of the delivery catheter 15 in a one-way deployment. A pusher member 19 may be advanced through the delivery catheter 15 to push the embolic device 10 out the distal end of the delivery catheter 15. An example pusher member 19 may have an enlarged distal end configured to push the proximal end 11 of the wire 12 to move the embolic device 10 out of the delivery catheter 15, as shown in FIG. 2. The pusher member 19 is not coupled to the embolic device 10, so any proximal movement of the pusher member 19 does not move the embolic device 10 in a proximal direction.

Figure 3:
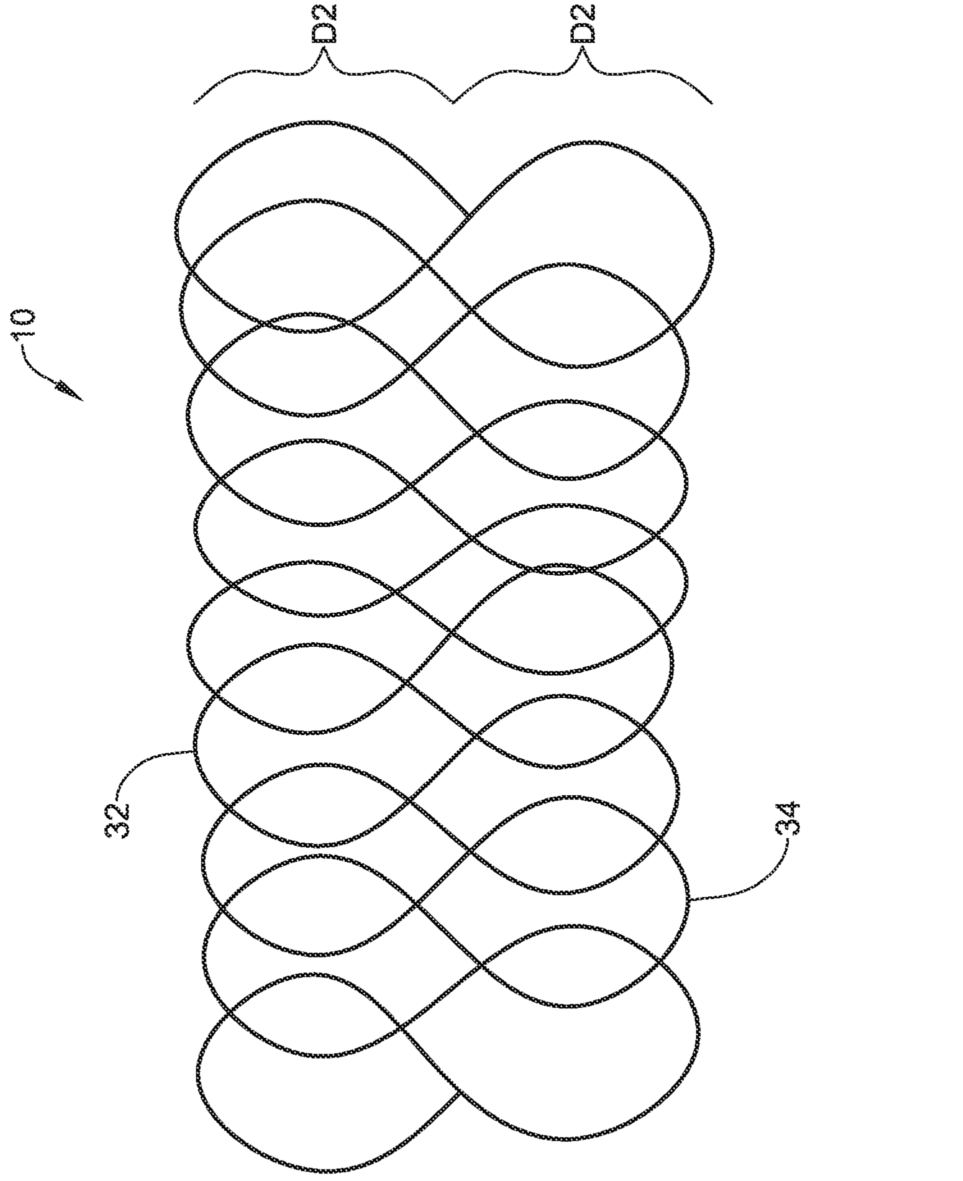
FIG. 3 is a side view of the embolic device of FIG. 2 in the secondary shape.

The embolic device 10 is shown completely in the secondary shape in FIG. 3, where the upper loops 32 longitudinally overlap adjacent upper loops 32 and the lower loops 34 longitudinally overlap adjacent lower loops 34. However, when in the secondary shape, the upper loops 32 do not overlap the lower loops 34. As seen in FIG. 3, when in the secondary shape, the longitudinally overlapping configuration of the embolic device 10 defines a series of longitudinally overlapping figure eights. When the embolic device 10 is formed from a helical coil 5, the upper loops 32 and lower loops 34 may each have a second outer diameter D2 larger than the first outer diameter D1 shown in FIG. 1B. In some embodiments, the second outer diameter D2 of the upper loops 32 may be the same as the second outer diameter D2 of the lower loops 34, and each of the second outer diameters D2 may be substantially the same, as shown in FIG. 3. In other embodiments, the upper loops 32 may have a larger or smaller outer diameter than the lower loops 34. In still further embodiments, each of the upper loops 32 and lower loops 34 may have a different, unique outer diameter.

Figure 4:
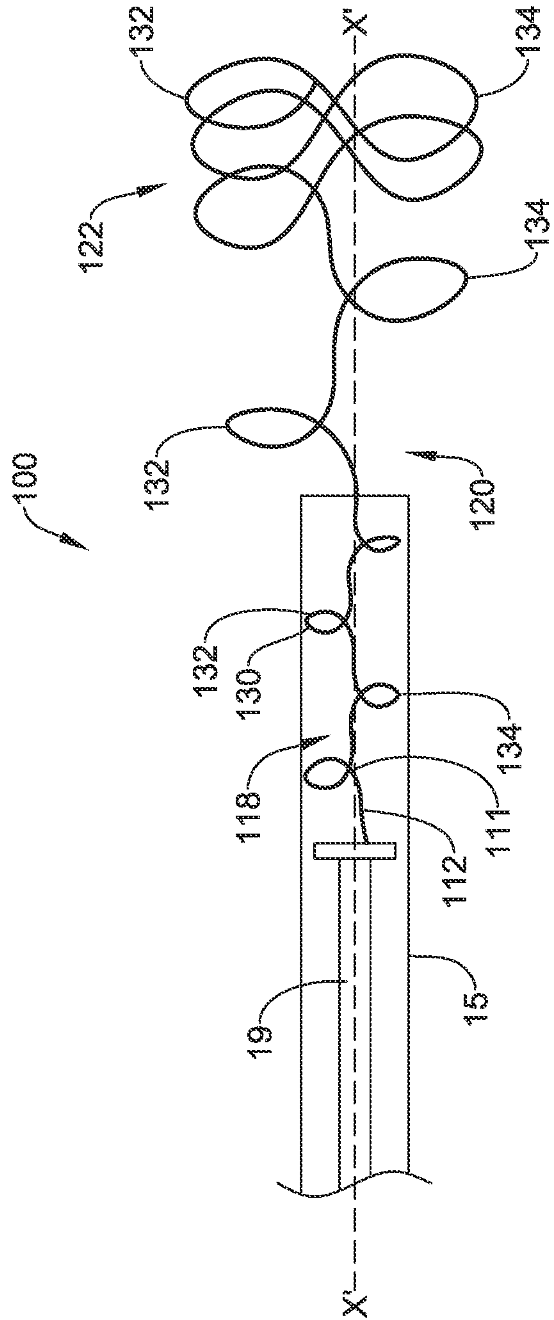
FIG. 4 is a side view of another example embolic device as it exits a delivery catheter and begins moving into the secondary shape, with the delivery catheter in cross-sectional view.

FIG. 4 illustrates another embodiment of embolic device 100 with a proximal region 118 constrained in a primary shape within a delivery catheter 15, a distal region 122 in a secondary shape outside the delivery catheter, and an intermediate region 120 transitioning from the primary shape to the secondary shape as it exits the delivery catheter. In some embodiments, the embolic device 100 may be formed from a single wire 112 such that the entire embolic device 100 is a monolithic structure. In other embodiments, the embolic device 100 may be formed from a plurality of wires 112 forming a plurality of secondary shapes. The wire 112 may automatically move from the primary shape to the predetermined secondary shape when the wire is released from the delivery catheter 15. In some embodiments, the wire 112 may be made of a nickel-titanium alloy (e.g., nitinol) which possesses both mechanical and thermal shape memory characteristics. In other embodiments, however, the wire 112 may be made of any material exhibiting mechanical and/or thermal shape memory characteristics or, alternatively, platinum, platinum alloys, tungsten, tungsten alloys, or other like materials. The wire 112 may be heat set or otherwise permanently set into the secondary shape. In some embodiments, the wire 112 may have a round cross section, with a diameter in a range of 0.05 mm to 0.3 mm.

The proximal region 118 has a primary shape defined by a plurality of loops 130 in a linearly expanded configuration, where all of the plurality of loops are longitudinally spaced apart and include upper loops 132 extending above a longitudinal axis X'-X' of the embolic device, and lower loops 134 extending below the longitudinal axis. At least some of the plurality of upper loops 132 and lower loops 134 in the primary shape are closed and are defined by a crossover point 111 of the wire 112. In the embodiment shown in FIG. 4, all of the loops 130 forming the embolic device 100 are closed loops with a first portion of the wire 112 crossing over a second portion of the wire 112 at crossover point 111 to form the closed loop 130. In the intermediate region 120, as the embolic device 100 exits the delivery catheter 15, the plurality of upper closed loops 132 move longitudinally closer together, and the lower closed loops 134 move longitudinally closer together. As shown in FIG. 4, the secondary shape is formed by longitudinally alternating upper closed loops 132 and lower closed loops 134. As the embolic device 100 continues moving distally beyond the delivery catheter 15, shown in the distal region 122, the plurality of upper loops 132 continue moving closer to one another until they longitudinally overlap one another, and the plurality of lower loops 134 continue moving closer to one another until they longitudinally overlap one another.

In some embodiments, a proximal end and/or region of the wire 112 may be devoid of any coupling structure configured to be removably engaged with a delivery device, as described above for coupling device 10. In some embodiments, the proximal end of the wire 112 may be an atraumatic end ground into a round shape or melted into a ball similar to the distal tip 14 described above. The embolic device 100 is instead pushed out of the delivery catheter 15 in a one-way deployment. A pusher member 19 may be advanced through the delivery catheter 15 to push the embolic device 100 out the distal end of the delivery catheter 15. An example pusher member 19 may have an enlarged distal end configured to push the proximal end of the wire 112 to move the embolic device 100 out of the delivery catheter 15, as shown in FIG. 4. The pusher member 19 is not coupled to the embolic device 100.

Figure 5:
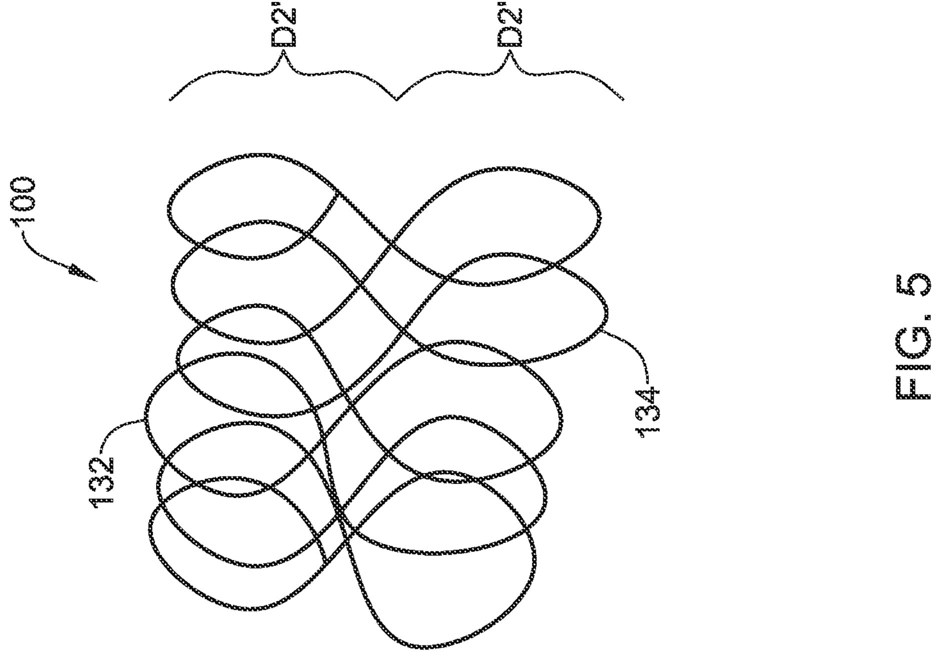
FIG. 5 is a side view of the embolic device of FIG. 4 in the secondary shape.

The embolic device 100 is shown completely in the secondary shape in FIG. 5, in which the upper closed loops 132 longitudinally overlap adjacent upper closed loops 132 and the lower closed loops 134 longitudinally overlap adjacent lower closed loops 134. However, when in the secondary shape, the upper closed loops 132 do not overlap the lower closed loops 134. As seen in FIG. 5, when in the secondary shape, the longitudinally overlapping configuration of the embolic device 100 defines a series of longitudinally overlapping figure eights with closed loops. When the embolic device 100 is formed from a helical coil 5, the upper loops 132 and lower loops 134 may each have a second outer diameter D2' larger than the first outer diameter D1 shown in FIG. 1B. In some embodiments, the second outer diameter D2' of the upper loops 132 may be the same as the second outer diameter D2' of the lower loops 134, and each of the second outer diameters D2' may be substantially the same, as shown in FIG. 5. In other embodiments, the upper loops 132 may have a larger or smaller outer diameter than the lower loops 134. In still further embodiments, each of the upper loops 132 and lower loops 134 may have a different, unique outer diameter.

In some embodiments of the embolic device 10, a proximal end and/or region of the wire 12 may be devoid of any coupling structure configured to be removably engaged with a delivery device. In some embodiments, the proximal end of the wire 12 may be an atraumatic end ground into a round shape or melted into a ball similar to the distal tip 14 described above. The embolic device 10 is instead pushed out of the delivery catheter 15 in a one-way deployment. A pusher member 19 may be advanced through the delivery catheter to push the embolic device 10 out the distal end of the delivery catheter 15. An example pusher member 19 may have an enlarged distal end configured to push the proximal end of the wire 12 to move the embolic device 10 out of the delivery catheter 15.

The materials that can be used for the various components of the embolic device 10, 100 for capturing lesion particles (and/or other systems or components disclosed herein) and the various elements thereof disclosed herein may include those commonly associated with medical devices. For simplicity purposes, the following discussion refers to the embolic device 10 (and variations, systems or components disclosed herein). However, this is not intended to limit the devices and methods described herein, as the discussion may be applied to other elements, members, components, or devices disclosed herein.

In some embodiments, the embolic device 10 (and variations, systems or components thereof disclosed herein) may be made from a metal, metal alloy, ceramics, zirconia, polymer (some examples of which are disclosed below), a metal-polymer composite, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; cobalt chromium alloys, titanium and its alloys, alumina, metals with diamond-like coatings (DLC) or titanium nitride coatings, other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super-elastic varieties, may exhibit distinct and useful mechanical properties. Linear elastic and/or non-super-elastic nitinol may be distinguished from super-elastic nitinol in that the linear elastic and/or non-super-elastic nitinol does not display a substantial "super-elastic plateau" or "flag region" in its stress/strain curve like super-elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super-elastic plateau and/or flag region that may be seen with super-elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super-elastic nitinol in that linear elastic and/or non-super-elastic nitinol may accept up to about 2-5% strain while remaining substantially elastic (e.g., before plastically deforming) whereas super-elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. For example, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a super-elastic alloy, for example a super-elastic nitinol can be used to achieve desired properties.

In at least some embodiments, portions or all of the embolic device 10 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the embolic device 10 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the embolic filtering device 200 (and variations, systems or components thereof disclosed herein) to achieve the same result.

In some embodiments, the embolic device 10 (and variations, systems or components thereof disclosed herein) and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex® high-density polyethylene, Marlex® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, Elast-Eon® from AorTech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An embolic device configured to be slidably received within and deployed from a catheter, the embolic device including a single wire having a primary shape when disposed within the catheter, and a secondary shape when released from the catheter, the single wire also having an intermediate shape when the single wire is transitioning from the primary shape to the secondary shape;

wherein the primary shape is defined by a plurality of loops in a linearly expanded configuration, where all of the plurality of loops are longitudinally spaced apart and do not longitudinally overlap, all of the plurality of loops including upper loops extending above a longitudinal axis of the embolic device, and lower loops extending below the longitudinal axis; and wherein in the secondary shape the upper loops and the lower loops are in a longitudinally overlapping configuration;

wherein the intermediate shape is different from the primary shape and the secondary shape is different from the intermediate shape.

2. The embolic device of claim 1, wherein in the secondary shape, the upper loops do not overlap the lower loops.

3. The embolic device of claim 1, wherein the longitudinally overlapping configuration defines a series of longitudinally overlapping figure eights.

4. The embolic device of claim 1, wherein the single wire is a helical coil of first loops, each of the first loops having a first outer diameter, each of the first outer diameters being substantially the same.

5. The embolic device of claim 4, wherein the upper loops and the lower loops each have a second outer diameter larger than the first outer diameter, wherein each of the second outer diameters is substantially the same.

6. The embolic device of claim 1, wherein the secondary shape is formed by longitudinally alternating upper and lower loops.

7. The embolic device of claim 6, wherein at least some of the plurality of loops in the primary shape are open and define a serpentine shape.

8. The embolic device of claim 6, wherein at least some of the plurality of loops in the primary shape are closed.

9. The embolic device of claim 6, wherein the upper and lower loops in the secondary shape are all closed.

10. The embolic device of claim 1, wherein the single wire automatically changes from the primary shape to the intermediate shape to the secondary shape when the single wire is released from the catheter.

11. The embolic device of claim 1, wherein the single wire is made from nitinol.

12. The embolic device of claim 1, wherein a cross section of the single wire is round, and a diameter of the cross section is in a range of 0.05 mm to 0.3 mm.

13. The embolic device of claim 1, wherein a distal end of the embolic device defines an atraumatic end, and a proximal end of the embolic device is devoid of any coupling element.

14. The embolic device of claim 1, wherein the embolic device further includes multiple fiber bundles coupled to the single wire.

15. A vascular occlusion system comprising:

a catheter having a lumen with a delivery end; and an embolic device configured to be slidably received within and deployed from the lumen of the catheter, the embolic device including a single wire having a primary shape when disposed in the lumen of the catheter, an intermediate shape when first released from the delivery end, and a final secondary shape;

wherein the primary shape is defined by a plurality of loops in a linearly expanded configuration, where all of the plurality of loops are longitudinally spaced apart and do not longitudinally overlap;

wherein in the secondary shape the plurality of loops includes upper and lower loops in a longitudinally overlapping configuration.

16. The vascular occlusion system of claim 15, wherein the longitudinally overlapping configuration is a series of longitudinally overlapping figure eights.

17. The vascular occlusion system of claim 15, wherein the secondary shape is formed by longitudinally alternating upper and lower loops.

18. The vascular occlusion system of claim 17, wherein at least some of the plurality of loops in the primary shape are open and define a serpentine shape.

19. The vascular occlusion system of claim 17, wherein at least some of the plurality of loops in the primary shape are closed.

20. A vascular occlusion system comprising:

a catheter having a lumen with a delivery end;

an embolic device configured to be slidably received within and deployed from the lumen of the catheter, the embolic device including a single wire having a primary shape when disposed in the lumen of the catheter, an intermediate shape when first released from the delivery end, final secondary shape, the primary shape defined by a plurality of loops in a linearly expanded configuration, where all of the plurality of loops are longitudinally spaced apart and do not longitudinally overlap, wherein in the secondary shape the plurality of loops include upper and lower loops in a longitudinally overlapping configuration; and a pusher member disposed within the lumen, the pusher member having a distal end configured to push a proximal end of the embolic device out of the lumen, wherein the pusher member and the embolic device are not coupled.

* * * * *